United States Patent [19]

Rupp et al.

[11] 4,096,182
[45] Jun. 20, 1978

[54] PROCESS FOR THE SIMULTANEOUS PREPARATION OF 2,5-DIOXO-1,2-OXA-PHOSPHOLANES AND β-HALOGENPROPIONIC ACID HALIDE

[75] Inventors: Walter Rupp, Königstein, Taunus; Manfred Finke, Kelkheim, both of Germany

[73] Assignee: Hoechst Aktiengesellschaft, Frankfurt am Main, Germany

[21] Appl. No.: 778,052

[22] Filed: Mar. 16, 1977

[30] Foreign Application Priority Data

Mar. 19, 1976 Germany .............................. 2611694

[51] Int. Cl.$^2$ .......................... C07C 51/58; C07F 9/02
[52] U.S. Cl. .............................. 260/544 Y; 260/545 P
[58] Field of Search ........................ 260/545 P, 544 Y

[56] References Cited

PUBLICATIONS

Chajrullin et al., Z. obsc. chim. vol. 37, pp. 710, 871 (1967), vol. 38, p. 288 (1968).

Primary Examiner—Gerald A. Schwartz
Attorney, Agent, or Firm—Curtis, Morris & Safford

[57] ABSTRACT

2,5-Dioxo-1,2-oxa-phospholanes of the formula (I)

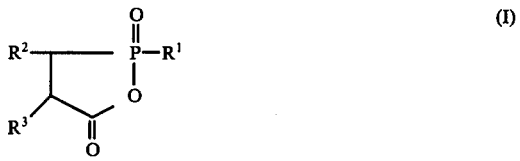

(I)

wherein $R^1$ is an organic radical and $R^2$ and $R^3$ each also represents an organic radical or hydrogen, are prepared by reacting 2-haloformylethyl-phosphinic acid halides of the formula (II)

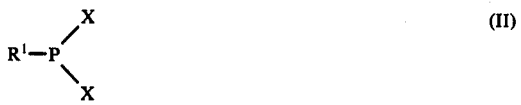

(II)

wherein $R^1$, $R^2$ and $R^3$ are defined as in formula (I) and X means Cl or Br, preferably Cl, with an approximatey equimolar quantity of acrylic acid. The compounds (II) may also be produced in the reaction batch and in situ by reacting about equimolar quantities of a dihalophosphine of the formula (III)

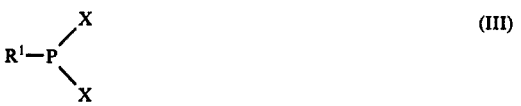

(III)

with an α,β-unsaturated acid (IV)

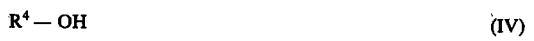

(IV)

In the formulae (III) and (IV) $R^1$, $R^2$, $R^3$ and X are defined as indicated above.

In the reaction there is formed, in addition to the compounds (I), practically exclusively β-halopropionic acid and no free hydrogen halide.

The phospholanes (I) are valuable flame retarding agents for plastics, intermediates, for example, for the synthesis of biocidals etc.

13 Claims, No Drawings

PROCESS FOR THE SIMULTANEOUS PREPARATION OF 2,5-DIOXO-1,2-OXA-PHOSPHOLANES AND β-HALOGENPROPIONIC ACID HALIDE

It is already known that 2-chloroformylethyl-phosphinic acid chlorides, which are readily accessible from alkyldichlorophosphines and α,β-unsaturated carboxylic acids, may be cyclized with acetic anhydride to 2,5-dioxo-1,2-oxa-phospholanes, acetyl chloride being formed as by-product. 2-Methyl- or 2,4-dimethyl-2,5-dioxo-1,2-oxa-phospholane may be obtained according to this process from the corresponding chloroformylalkyl-phosphinic acid chlorides in a yield of 84.3 or 78.6% respectively.

When the yields are calculated on methyldichlorophosphine, which reacts with acrylic acid or methacrylic acid to yield the corresponding 2-chloroformylalkyl-methylphosphinic acid chlorides, there results a total yield of 67.7% or 60.7% for the 2-methyl- or 2,4-dimethyl-2,5-dioxo-1,2-oxa-phospholane respectively (cf. V. K. Charjrullin, I. I. Sobcuk and A. N. Pudovik, Z.obsc.chim. 37, 710 (1967); V. K. Chajrullin, R. M. Kondrat'eva and A. N. Pudovik, Z.obsc.chim. 38, (1968)).

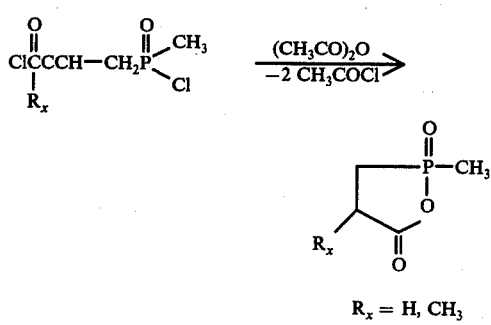

$R_x = H, CH_3$

It is further known that (2-chloroformyl-2-methyl)-ethylphenyl-phosphinic acid chloride cyclizes with molar quantities of acetic acid to 2-phenyl-4-methyl-2,5-dioxo-1,2-oxa-phospholane in a yield of 71.8%. When this yield is calculated on phenyldichlorophosphine reacting with methacrylic acid to yield the corresponding 2-chloroformylethyl-phosphinic acid chloride, the total yield of 2,5-dioxo-1,2-oxa-phospholane amounts to 50.5%. Acetyl chloride and hydrogen chloride are formed thereby as by-products (cf. V. K. Chajrullin, V. N. Eliseenkov, A. N. Pudovik, Z.obsc.chim. 37, 871 (1967)).

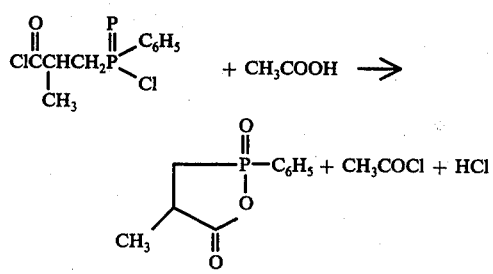

In both processes 2-chloroformylethyl-phosphinic acid chlorides are first isolated and then cyclized in a separate step with acetic anhydride or acetic acid. When using acetic acid as cylization reactant, 1 mol of hydrogen chloride is obtained, which is an undesired by-product.

The formation of hydrogen halide cannot be avoided either in the process for the preparation of 2,5-dioxo-1,2-oxa-phospholanes, proposed in the patent application Ser. No. 699 256 wherein dihalogenphosphines are directly reacted with α,β-unstarated carboxylic acids in a single course reaction, i.e. without isolation of the intermediary formed 2-halo-formylethylphosphinic acid halides using as cyclization agents, for example H$_2$O, carboxylic acids, phosphinic acids etc.

The present invention is based on the observation that the formation of hydrogen halide in the preparation of 2,5-dioxo-1,2-oxa-phospholanes can be avoided when using acrylic acid as cyclization agent for 2-haloformylethyl-phosphinic acid halides.

It has been found that 2,5-dioxo-1,2-oxa-phospholanes of the formula (I)

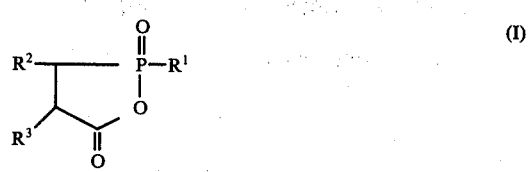

wherein R$^1$ is an alkyl group with up to 18 carbon atoms, preferably 1 to 12, especially 1 to 4, carbon atoms which may be substituted, preferably by three, especially by one, halogen atoms, especially chlorine, a cycloalkyl group with up to 8 carbon atoms, especially cyclopentyl, cyclohexyl, an alkenyl group with up to 8 carbon atoms, especially vinyl and allyl, an aryl group with up to 14 carbon atoms, especially phenyl, which may be substituted by lower alkyl groups with up to 4 carbon atoms, lower alkoxy groups with up to 4 carbon atoms, halogen or by amino groups alkylated or dialkylated by lower alkyl radicals with up to 4 carbon atoms, preferably up to two times, or an aralkyl group with up to 15 carbon atoms, especially benzyl, which may be substituted in analogous manner to the aryl group, R$^2$ is an alkyl group with up to 4 carbon atoms, preferably methyl or hydrogen and R$^3$ is an alkyl radical with up to 6 carbon atoms, especially methyl, a phenyl radical, which may be subtituted by halogen, preferably chlorine, or lower alkyl groups with up to 4 carbon atoms, preferably methyl, up to three times, preferably once or twice, a benzyl radical or hydrogen, especially methyl or hydrogen, at least one of the readicals R$^2$ and R$^3$ standing preferably for a hydrogen atom, can be obtained by reacting 2-haloformylethyl-phosphinic acid halides of the formula (II)

wherein R$^1$, R$^2$ and R$^3$ are defined as in formula (I) and X stands for chlorine or bromine, preferably chlorine with an approximately equimolar quantity of acrylic acid.

It is surprising that β-halogenopropionic acid halide is formed nearly exclusively in addition to 2,5-dioxo-1,2-oxaphospholane of the formula (I) in the cyclization of 2-halogenoformylethyl-phosphinic acid halides of the formula (II). According to what had been expected an equimolar mixture of acrylic acid halide and hydrogen halide should have formed instead of β-halogenopropionic acid halide, since the addition of hydrogen chloride, for example, to acrylic acid chloride, is not successful under the reaction conditions.

Suitable starting compounds of the formula (II) are the following 2-halogenoformylethyl-phosphinic acid halides, for example:

2-chloroformylethyl-methyl-phosphinic acid chloride,
2-chloroformylethyl-ethyl-phosphinic acid chloride,
2-chloroformylethyl-propyl-phosphinic acid chloride,
2-chloroformylethyl-butyl-phosphinic acid chloride,
2-chloroformylethyl-hexyl-phosphinic acid chloride,
2-chloroformylethyl-octyl-phosphinic acid chloride,
2-chloroformylethyl-dodecyl-phosphinic acid chloride,
2-chloroformylethyl-hexadecyl-phosphinic acid chloride,
2-chloroformylethyl-octadecyl-phosphinic acid chloride,
2-chloroformylethyl-chloromethyl-phosphinic acid chloride,
2-chloroformylethyl-chloropropyl-phosphinic acid chloride,
2-chloroformylethyl-vinyl-phosphinic acid chloride,
2-chloroformylethyl-allyl-phosphinic acid chloride,
2-chloroformylethyl-propenyl-phosphinic acid chloride,
2-chloroformylethyl-octenyl-phosphinic acid chloride,
2-chloroformylethyl-benzyl-phosphinic acid chloride,
2-chloroformylethyl-phenyl-phosphinic acid chloride,
2-chloroformylethyl-naphthyl-phosphinic acid chloride,
2-chloroformylethyl-anthryl-phosphinic acid chloride,
2-chloroformylethyl-p-chlorophenyl-phosphinic acid chloride,
2-chloroformylethyl-cyclohexyl-phosphinic acid chloride,
2-chloroformylethyl-cyclooctyl-phosphinic acid chloride,
(2-chloroformyl-1-methyl-ethyl)-methyl-phosphinic acid chloride,
(2-chloroformyl-1-methyl-ethyl)-ethyl-phosphinic acid chloride,
(2-chloroformyl-1-methyl-ethyl)-propyl-phosphinic acid chloride,
(2-chloroformyl-1-methyl-ethyl)-dodecyl-phosphinic acid chloride,
(2-chloroformyl-1-methyl-ethyl)-octadecyl-phosphinic acid chloride,
(2-chloroformyl-1-butyl-ethyl)-hexadecyl-phosphinic acid chloride,
(2-chloroformyl-1-methyl-ethyl)-vinyl-phosphinic acid chloride,
(2-chloroformyl-1-methyl-ethyl)-phenyl-phosphinic acid chloride,
(2-chloroformyl-1-phenyl-ethyl)-methyl-phosphinic acid chloride,
(2-chloroformyl-2-methyl-ethyl)-methyl-phosphinic acid chloride,
(2-chloroformyl-2-methyl-ethyl)-hexyl-phosphinic acid chloride,
(2-chloroformyl-2-propyl-ethyl)-dodecyl-phosphinic acid chloride,
(2-chloroformyl-2-hexyl-ethyl)-octadecyl-phosphinic acid chloride, as well as the corresponding 2-carboxyethyl-phosphinic acid bromides.

The 2-haloformylethyl-phosphinic acid halides can be readily prepared from the corresponding alkyldihalophosphines and α,β-unsaturated carboxylic acids according to Russian Pat. No. 173,763. The phosphine-carboxylic acid halides thus obtained can be used as crude products without further purification.

The process according to the invention is generally carried out by reacting about equimolar quantities of acrylic acid with 2-haloformylethyl-phosphinic acid halides. Thereby the acrylic acid can be added dropwise to phosphinic acid dihalide, preferably -dichloride or vice versa, the dihalide may be added to the acrylic acid. The reaction may be carried out advantageously under a slightly elevated pressure, whereby a dropping funnel with pressure equalizator, for example can be used and the reflux condenser of the reaction vessel can be connected with a tube which is immersed about 5 to 60 cm in a sealing liquid, for example, paraffin or mercury. The elevated pressure to be applied is not critical and may be in the range of from fragments of one atmosphere to several atmospheres.

Inert solvents, for example dioxane, tetrahydrofuran, 1,2-dimethoxyethane, methylene chloride, 1,2-dichloroethane, or toluene may be used.

In some cases it may be advantageous and even preferable to carry out the reaction in an inert gas atmosphere, for example of nitrogen.

The process can be carried out discontinuously or continuously, at a temperature of from about −20° to +100° C, preferably of from 0° C to +80° C, especially of from +20° C to +60° C. The reaction time is in the range of from about 1 to 6 hours.

The process according to the invention can be carried out especially advantageously in the following manner: The haloformyl compound of the formula (II) is first produced in situ in known manner by reacting about equimolar quantities of a dihalophosphine of the formula $R^1PhaI_2$ (III) with acrylic acid or a substituted acrylic acid of the formula $CHR^2=CR^3—COOH$, wherein $R^1$, $R^2$ and $R^3$ are defined as in formula (I) and hal means chlorine or bromine, preferably chlorine, at a temperature especially of from 15° to 60° C and the reaction mixture formed substantially consisting of the corresponding haloformyl compound of the formula (II) is further reacted immediately, at the same temperature or at a higher reaction temperature, preferably of up to +80° C, especially of from 20° to 60° C, in the above described manner, with an approximately equimolar quantity of acrylic acid. The sequence of addition of each reactant in both steps of the single course process is not critical. If acrylic acid is used as acid of the formula (IV), the dihalophospine of the formula (III) is preferably added to the double molar quantity of acrylic acid.

Suitable dihalophosphines of the formula (III) are, by way of example:
methyldichlorophosphine, ethyldichlorophosphine, propyldichlorophosphine, butyldichlorophosphine, dodecyldichlorophosphine, chloromethyldichlorophosphine, vinyldichlorophosphine, cyclohexyldichlorophosphine, benzyldichlorophosphine, phenyldichlorophosphine, p-chlorophenyldichlorophosphine etc. and the corresponding dibromophosphines.

Examples of suitable acrylic acids are:

methacrylic acid, crotonic acid, 1-ethylacrylic acid, 1-phenylacrylic acid etc.

The reaction mixture obtained in the process of the invention is separated generally under reduced pressure by fractional distillation. Thereby β-chloropropionic acid chloride is advantageously distilled off at about 4 to 40 torrs, since possibly formed small qantities of acrylic acid chloride do not further condense under these conditions and at a temperature of the cooling water of from about 5° to 20° C and thus they can be readily separated by collecting them in a vessel cooled with dry ice which is subsequent to the distillation column. When working under a pressure of more than 40 torrs, the transition temperature of β-chloropropionic acid chloride and especially the temperature of the bottom product are so high that an increased splitting off of hydrogen halide with simultaneous formation of acrylic acid halide must be taken into account.

The reaction mixture can also be separated by extracting β-halopropionic acid halide with in inert solvent, for example petrol ether, cyclohexane, benzene or toluene, or by mixtures of such solvents. The 2,5-dioxo-1,2-oxa-phospholanes, which are practicably insoluble in these solvents, can be further purified by crystallization or distillation.

The yields of 2,5-dioxo-1,2-oxa-phospholanes are in the range of from about 85° to 95° C and of β-halopropionic acid chloride in the range of from about 70 to 75% of the theory, i.e. calculated on the dihalophosphine compound used of the formula (III). The process according to the present invention presents a considerable technical progress, as it makes it possible to prepare 2,5-dioxo-1,2-oxa-phospholanes even from crude, non purified 2-haloformylethyl-phosphinic acid halides in a high yield and furthermore β-chloropropionic acid chloride, for example, is obtained, which is not accessible by direct addition of hydrogen chloride to acrylic acid chloride in the absence of catalysts. 2,5-dioxo-1,2-oxa-phospholanes are valuable flame-retarding agents, for example for plastics and they can be used, for example for the preparation of flame-resistant linear polyester. They are furthermore valuable intermediates, which may be processed to flame-retarding agents, for example for polyolefins. Finally they are important intermediates for the synthesis of biocidals.

β-Chloropropionic acid chloride is the starting material, for example for the preparation of acrylic acid esters and for organic syntheses.

The following examples illustrate the invention:

EXAMPLE 1

2-Methyl-2,5-dioxo-1,2-oxa-phospholane 72 g (1 mol) of acrylic acid are added dropwise to 117 g (1 mol) of methyldichlorophosphine, at a temperature of from 20° to 30° C for a period of about 1 hour. The mixture is stirred at 30° C for 15 minutes and 72 g (1 mol) of acrylic acid are again added dropwise to 2-chloroformylethylmethylphosphinic acid chloride formed, at the same temperature. After completion of the addition the reaction solution is maintained at 40° C for 30 minutes and then separated by distillation in vacuo. 89 g of β-chloropropionic acid chloride (70% of the theory) are obtained at a boiling point $Bp_{11}$, which corresponds to 43° C and 114 g 2-methyl-2,5-dioxo-1,2-oxa-phospholane (85.1% of the theory) at a boiling point $Bp_{0.6}$, which corresponds to 165° – 167° C.

EXAMPLE 2

2-Methyl-2,5-dioxo-1,2-oxa-phospholane 72 g (1 mol) of acrylic acid are added dropwise at a slightly elevated pressure to 58.5 (0.5 mol) of methyldichlorophosphine at a temperature of from 30° to 35° C within a period of 2 hours, using a dropping funnel with pressure equalizer. The reflux condenser of the reaction flask is thereby connected with a glass tube which immerses about 40 cm in liquid paraffin. After completion of the addition the reaction mixture is stirred for about 2 hours at 60° C. 48 g of β-chloropropionic acid chloride (76% of the theory) are obtained thereafter by distillation in vacuo at 6 torrs and 65 g of 2-methyl-2,5-dioxo-1,2-oxa-phospholane (97% of the theory) remain, which crystallize when cooling.

EXAMPLE 3

2-Methyl-2,5-dioxo-1,2-oxa-phospholane 117 g (1 mol) of methyldichlorophosphine are added dropwise to 144 g (2 mols) of acrylic acid in the manner described in Example 2, at a slightly elevated pressure, at a temperature of from 25° to 30° C within 2 hours. After completion of the addition, the mixture is stirred for 2 hours at 70° C and β-chloropropionic acid chloride is distilled off thereafter under reduced pressure. 95 g of β-chloropropionic acid chloride (76% of the theory) are obtained and 122 g of crystalline 2-methyl-2,5-dioxo-1,2-oxa-phospholane (91% of the theory).

EXAMPLE 4

2,4-Dimethyl-2,5-dioxo-1,2-phospholane 8.4 g (0.117 mol) of acrylic acid are added dropwise to 23.8 g (0.117 mol) of (2-chloro-formyl-1-methylethyl)-methylphosphinic acid chloride at a temperature of from 25° to 30° C at a slightly elevated pressure, in the manner described in Example 2, for a period of about 30 minutes. Thereafter the mixture is stirred for 2 hours at 60° C and separated subsequently by distillation in vacuo. 10.5 g of β-chloropropionic acid chloride (70% of the theory) are obtained at a boiling point $B_{p6}$, which corresponds to 31° C and 17 g of 2,4-dimethyl-2,5-dioxo-1,2-oxa-phospholane (85.5% of the theory) at a boiling point $B_{p0.6}$, which corresponds to 150° C.

COMPARATIVE EXAMPLE 25 g (about 0.7 mol) of gaseous hydrogen chloride are introduced into 45 g (0.5 mol) of acrylic acid chloride at 50° C for a period of 6 hours. The batch is allowed to stand over night. Thereafter it is distilled at about 20 torrs. 3 g (4.7% of the theory) of β-chloropropionic acid chloride and 39 g (87% of the theory) of acrylic acid chloride are obtained, the latter being condensed in a recipient cooled with dry ice.

What is claimed is:

1. A process for the preparation of 2,5-dioxo-1,2-oxa-phospholanes of the formula (I)

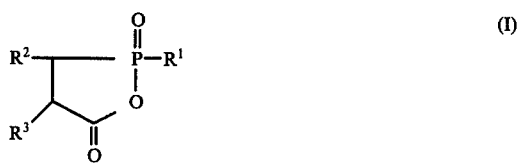

wherein $R^1$ is an alkyl group with up to 18 carbon atoms which may be substituted by up to three halogen atoms, a cycloalkyl group with up to 8 carbon atoms, an alkenyl group with up to 8 carbon atoms, an aryl group with up to 14 carbon atoms, which may be substituted by lower alkyl groups with up to 4 carbon atoms, lower alkoxy groups with up to 4 carbon atoms, halogen or with amino groups alkylated or dialkylated by lower alkyl radicals with up to 4 carbon atoms or an aralkyl group with up to 15 carbon atoms, which may be substituted in analogous manner to the aryl group, $R^2$ is an alkyl group with up to 4 carbon atoms, or hydrogen and $R^3$ is an alkyl group with up to 6 carbon atoms, a phenyl radical, which may be substituted up to three times by halogen or by lower alkyl groups with up to 4 carbon atoms, a benzyl radical or hydrogen, with simultaneous preparation of about equimolar quantities of a β-halopropionic acid halide, which comprises reacting a 2-haloformylethylphosphinic acid halide of the formula (II)

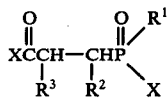
(II)

wherein $R^1$, $R^2$ and $R^3$ are defined as in formula (I) and X stands for chlorine or bromine with an approximately equimolar quantity of acrylic acid.

2. Process as claimed in claim 1, which comprises carrying out the reaction at a temperature in the range of from −20° to +100° C.

3. Process as claimed in claim 1 which comprises carrying out the reaction in the presence of an inert solvent.

4. Process as claimed in claim 1 which comprises carrying out the reaction in an inert gas atmosphere.

5. Process as claimed in claim 1 which comprises carrying out the reaction at a slightly elevated pressure.

6. Process as claimed in claim 1 which comprises producing the haloformyl compound of the formula (II) in situ by reacting about equimolar quantities of a dihalophosphine of the formula $R^1Phal_2$ (III) with acrylic acid or a substituted acrylic acid of the formula (CHR=CR—COOH (IV), wherein $R^1$, $R^2$ and $R^3$ are defined as in formula (I) and hal means chlorine or bromine at a temperature in the range of from 15° to 50° C and further reacting immediately the reaction mixture thus obtained, which substantially consists of the corresponding haloformyl compound of the formula (II), at the same temperature or at a higher temperature up to 100° C., with an approximately equimolar quantity of acrylic acid.

7. Process as claimed in claim 6, which comprises adding the dihalophosphine of the formula (III) to double the molar quantity of acrylic acid of the formula (IV), wherein $R^2$ and $R^3$ represent hydrogen.

8. Process as claimed in claim 1 which comprises separating the reaction mixture by distillation under reduced pressure.

9. Process as claimed in claim 1 which comprises separating the reaction mixture by extraction with an inert solvent.

10. Process as defined in claim 1 wherein $R^1$ is methyl and $R^2$ and $R^3$ are hydrogen.

11. Process as defined in claim 1 wherein $R^1$ and $R^3$ are methyl and $R^2$ is hydrogen.

12. Process as defined in claim 2 wherein the temperature is from 0° to 80° C.

13. Process as defined in claim 2 wherein the temperature is from 20° to 60° C.

* * * * *